(12) United States Patent
Gorenstein

(10) Patent No.: US 6,312,575 B1
(45) Date of Patent: Nov. 6, 2001

(54) METHODS AND DEVICES FOR CHROMATOGRAPHIC PATTERN ANALYSIS EMPLOYING CHROMATOGRAPHIC VARIABILITY CHARACTERIZATIONS

(75) Inventor: Marc V. Gorenstein, Needham, MA (US)

(73) Assignee: Waters Investments Limited

( * ) Notice: Subject to any disclaimer, the term of this patent is extended or adjusted under 35 U.S.C. 154(b) by 0 days.

(21) Appl. No.: 09/326,933

(22) Filed: Jun. 7, 1999

Related U.S. Application Data

(63) Continuation of application No. 08/936,168, filed on Sep. 23, 1997, now Pat. No. 5,969,228, which is a continuation-in-part of application No. 08/631,446, filed on Apr. 12, 1996, now abandoned.

(51) Int. Cl.$^7$ .................................................... B01D 57/02
(52) U.S. Cl. ............................................. 204/450; 96/103
(58) Field of Search ............................... 204/450; 96/103

(56) References Cited

U.S. PATENT DOCUMENTS

| | | |
|---|---|---|
| 4,353,242 | 10/1982 | Harris . |
| 4,740,903 | 4/1988 | Nakatsuka . |
| 4,835,708 | 5/1989 | Frans . |
| 5,446,575 | 8/1995 | Lysakowski . |

FOREIGN PATENT DOCUMENTS

| | | |
|---|---|---|
| 0 665 433 A1 | 8/1995 | (EP) . |
| WO 93/21592 | 10/1993 | (WO) . |

OTHER PUBLICATIONS

Andersson, Roger, Simplex Focusing of Retention Times and Latent Variable Projection SOF Chromatographic Profiles, 8386 Chemometrics and Intelligent Laboratory Systems (Jan. 22, 1994), No. 1, Amsterdam, NL.

Malmquist, G., Danielsson, R., Alignment of Chromatographic Profiles for Principal Component Analysis, Journal of Chromatography A. 687 (1994) 71–88.

Mason, J., Kirk, I., Windosr, C., A Novel Algorithm for Chromatogram Matching in Qualitative Analysis, Journal of High Resolution Chromatography, vol. 15, Aug. 1992.

Malmquist, G., Multivariate Evaluation of Peptide Mapping Using the Entire Chromatographic Profile, J. Chromatography, A 687 (1994) 89–100.

Tejada, S., Sigsby, J., Identification of Chromatographic Peaks Using Lotus 1–2–3, Journal of Chromatographic Science, vol. 26, Oct. 1988.

Elling, J., Mniszewski, Susan M. and Zahrt, John D., Automated Chromatographic Data Interpretation Using an Expert System, Journal of Chromatographic Science vol. 32, Jun. 1994.

Glickman, S., Kilburn, J., Butler, W., Ramos, L., Rapid Identification of Mycolic Acid Patterns of Mycobacteria by High–Performance Liquid Chromatography Using Pattern Recognition Software and a Mycobacterium Library, Journal of Clinical Microbiology, Mar. 1994, p. 740–745.

Savitzky, Abraham and Golay, Marcel J.E., Smoothing and Differentiation of Data by Simplified Least Squares Procedures, Analytical Chemistry, Jul. 1964, vol. 36, No. 8, pp. 1627–1639.

Strang, Gilbert, Introduction to Applied Mathetmatics, Wellesley–Cambridge Press, copyright 1986, Mass Institute of Technology, p. 37, Chapter 1, Symmetric Linear Systems, Section 1,4 Minimum Principles.

Miller, J.C. and Miller, J. N., Statsistics for Anlaytical Chemistry, Ellis Horwood Series in Analytical Chemistry, Second Edition 1988, Chapter 3, Significance Tests, pp. 53–80.

*Primary Examiner*—Scott W. Houtteman
(74) *Attorney, Agent, or Firm*—Brian L. Michaelis

(57) ABSTRACT

Method and devices for performing chromatographic pattern analysis determine chromatographic variability due to a plurality of sources without requiring identification or characterization of peaks or other chromatographic features, receives data indicative of a standard chromatogram and a first sample chromatogram generated from a first mixture by a High Pressure Liquid Chromatography (HPLC) device and data indicative of a plurality of additional sample chromatograms generated by the HPLC device from a plurality of different mixtures. The method and devices generate from the standard chromatogram, a plurality of sets of chromatographic variability data, each set being indicative of a different effect of the chromatographic variability of the HPLC. The standard chromatogram is modified as a function of the variability data, and a residual value, indicative of a difference between the modified standard chromatograms and the first sample chromatogram is generated. Residual values are generated for the additional sample chromatograms and are used to determine differences between the corresponding mixtures and the first mixture.

5 Claims, 7 Drawing Sheets

METHODS AND DEVICES FOR CHROMATOGRAPHIC PATTERN ANALYSIS EMPLOYING CHROMATOGRAPHIC VARIABILITY CHARACTERIZATIONS

AUTHORIZATION

This application is a continuation of Ser. No. 08/936,168, filed Sep. 23, 1997 now U.S. Pat. No. 5,969,228 which is a continuation-in-part of a prior application Ser. No. 08/631,446 filed, Apr. 12, 1996, now abandoned.

A portion of the disclosure of this patent document contains material which is subject to copyright protection. The copyright owner has no objection to the facsimile reproduction by anyone of the patent document or the patent disclosure, as it appears in the Patent and Trademark Office patent file or records.

FIELD OF THE INVENTION

This invention relates in general to the field of analysis of chromatograms and more particularly, though not limited to, determining chromatographic variability in order to increase the accuracy of chromatographic analysis.

BACKGROUND OF THE INVENTION

Chromatography is a technique widely used in the analysis of multi-component substances. In chromatography, a liquid or gas, of known or unknown composition, is injected into a chromatograph which generates a chromatogram in the form of a two dimensional graph in which absorptivity of the injected liquid, or conductivity of the injected gas or some other physical response is plotted against time. The absorptivity of the liquid or conductivity of the gas with respect to time as it passes through the chromatograph is indicative of the composition of the liquid or gaseous mixture.

Common uses of chromatography include quality control, in which manufactured substances are analyzed to verify the composition, and qualitative and quantitative analysis in which chromatograms derived from unknown substances are generated to analyze and determine the composition of the substance. In a quality control application, a chromatogram of a known and desired substance is generated and compared to the chromatogram of the manufactured substance. In qualitative and quantitative analysis applications, one or more chromatograms are generated of the unknown substance in an attempt to identify the components or quantify the amounts of each of the components of the substance.

In either of the above applications, the chromatogram(s) must be analyzed to determine similarities or differences with other chromatograms. Typically, such analysis requires analysis and comparison of the peaks, including the retention time, height and area of peaks between one chromatogram with those of another. In order to perform such a comparison, a method of identifying the peaks to be compared must be developed and optimized, and then a method to compare the peaks and other above identified aspects of the chromatograms must be developed. Principal Component Analysis (PCA) is one such technique and is referred to by G. Malmquist and R. Danielsson in a paper entitled "Alignment of Chromatographic Profiles for Principal Component Analysis: A Prerequisite for Fingerprinting Methods", *Journal of Chromatography A*, 687 (1994) 71–88. As described by Malmquist and Danielsson, retention times of selected peaks are used to align corresponding chromatograms. Once they are aligned, the absorbances are themselves compared. Another technique is described by J. P. Mason et al. in an article entitled "A Novel Algorithm for Chromatogram Matching in Qualitative Analysis", *Journal of high Resolution Chromatography*, v. 15, pp. 539–547 (August 1992) which describes an automated chromatographic matching technique which compares only peak heights, areas and retention times.

Chromatographic analysis must also take into account variability introduced by the chromatograph such as baseline drift, retention time wander and concentration change. Such variations of the chromatograph are manifested as variations in the chromatograms generated by the chromatograph and further complicate the analysis by requiring the analysis to take into account those several variations. In the above referenced paper by Malmquist and Danielsson, a technique is described for compensating for chromatographic variability in the context of enhancing chromatographic analysis by PCA Known techniques for chromatographic analysis such as described by Malmquist and Danielsson and Mason et al. typically require the steps described above of specifying a method of identifying peaks to be compared, specifying a method of comparing the various aspects of the peaks, and then actually performing the comparisons, while taking into account the effects of chromatographic variability. Although computerized techniques such as those described by Mason are helpful in performing such tasks, many known techniques continue to be time consuming, sometimes tedious and require the skills of highly trained personnel.

It is accordingly an object of the present invention to provide a computation devices or systems for chromatographic analysis which compensate for chromatographic variability and which perform chromatographic analysis without requiring the characterization of peaks or other chromatographic features as required by known techniques.

SUMMARY OF THE INVENTION

Embodiments of the present invention are directed to devices and methods for performing chromatographic analysis. As used herein, the term "chromatographic analysis device" refers to computers and computational apparatus for receiving and processing data; and, software and programming which directs such computers and computational apparatus for receiving and processing data.

In accordance with the primary object of the invention, a chromatographic analysis method employs a chromatogram alignment procedure which characterizes variability of a chromatograph. In accordance with a further object of the invention, the chromatographic analysis method employs the characterized chromatographic variability in the comparison of chromatograms. Advantageously, the chromatographic analysis method of the present invention compares chromatograms as patterns and does not require the characterization of peaks or the identification of the accompanying peak lift-off or touch down points. Moreover, peak heights, areas or retention times need not be computed. The phrase "characterization of peaks" is intended to refer to the process of peak integration which requires identification of the baseline by identification of the lift and touchdown points of the peak in question and then actual integration of the peak. The chromatographic pattern analysis method of the present invention applies to chromatograms obtained by isocratic or gradient chromatographic separations. In isocratic chromatography, the composition of the solvent is held constant throughout the chromatographic separation. In gradient chromatography, the composition of the solvent is varied in a predetermined way to obtain enhanced control over the retention times of compounds.

In a first aspect, a chromatographic analysis method operating in accordance with the principles of the present invention determines differences between a standard chromatogram and a sample chromatogram. The standard chromatogram is represented by a set of standard data points, indicative of the standard chromatogram over a selected elution time range and the sample chromatogram is represented by a set of sample data points indicative of the sample chromatogram over the same elution time range or an elution time range offset by a fixed amount. The standard data points and the sample data points are each generated by sampling each respective chromatogram at a fixed rate. The chromatographic analysis method then generates a plurality of sets of chromatographic variability data points from the standard data points, each of the sets of chromatographic variability data points being indicative of effects of a predetermined source of chromatographic variability on the standard chromatogram. The method also generates a set of modified standard data points, which correspond to the standard data points modified as a function of the chromatographic variability data points, to model chromatographic variability of a chromatograph which generates said chromatograms.

The method described above may be used with standard and sample chromatograms generated from the same mixtures in order to determine variability of the chromatograph. In addition, the method may be used to determine similarities or differences between the standard chromatogram and sample chromatograms from different or unknown mixtures. To assist in such a comparison, the method, in a second aspect, generates residue values which are indicative of differences between the standard chromatogram and the sample chromatograms. The residue value generated from a comparison of the standard to sample chromatograms of the same mixture may then be compared to residue values generated from a comparison of standard and sample chromatograms of different mixtures to determine whether the mixtures corresponding to the sample and the standard chromatograms are the same or different mixtures.

The chromatographic variability data points derived from the standard chromatogram allow the standard chromatogram to be modified to reflect a broad range of possible chromatograms that differ from the standard only by the effects of chromatographic variability.

The method uses the chromatographic variability data points derived from the standard to find a model chromatogram that most closely matches the sample chromatogram. In this sense, the method measures chromatographic variability reflected in the sample by modifying the standard chromatogram.

Scale factors generated as a function of the chromatographic variability data points, that describe this "best-fit" model chromatogram are one measure of chromatographic variability between the standard and sample. The resultant difference between the model and the sample is another measure. These are both advantageously measures of chromatographic variability in the sense that the method determines how much variability has to be applied to the standard chromatogram (through the use of the chromatographic variability data points) to get the model based on the standard chromatogram to match the sample chromatogram.

The chromatographic variability data points derived from the standard chromatogram need only be generated once for each standard and can advantageously be used repeatedly in determining the variabilities between the standard and multiple sample chromatograms.

Embodiments operating in accordance with the principles summarized above advantageously provide an accurate determination of chromatographic variability without requiring identification or characterization of particular peaks or other features of the chromatograms in question. When chromatograms are from the same or similar mixtures chromatographic variability due to baseline drift, retention time wander and concentration change are measured and removed regardless of the particular features of the chromatogram in question and without additional calibration of the chromatograph or addition of reference compounds to the mixtures in question. In a preferred embodiment, the chromatographic analysis system removes chromatographic variability due to concentration change, retention time offset, retention time stretch, baseline offset and baseline slope. In other embodiments, the method may remove chromatographic variability due to only one of the above mentioned sources of chromatographic variability of different subsets of such sources.

A further embodiment of the present invention features a chromatographic analysis device. The device receives and processes data in the manner described with respect to the method.

These and other features and advantages of the present invention may be better understood by considering the following detailed description of certain preferred embodiments of the invention. In the course of this description, reference will be made to the attached drawings.

DETAILED DESCRIPTION

Figure 1:
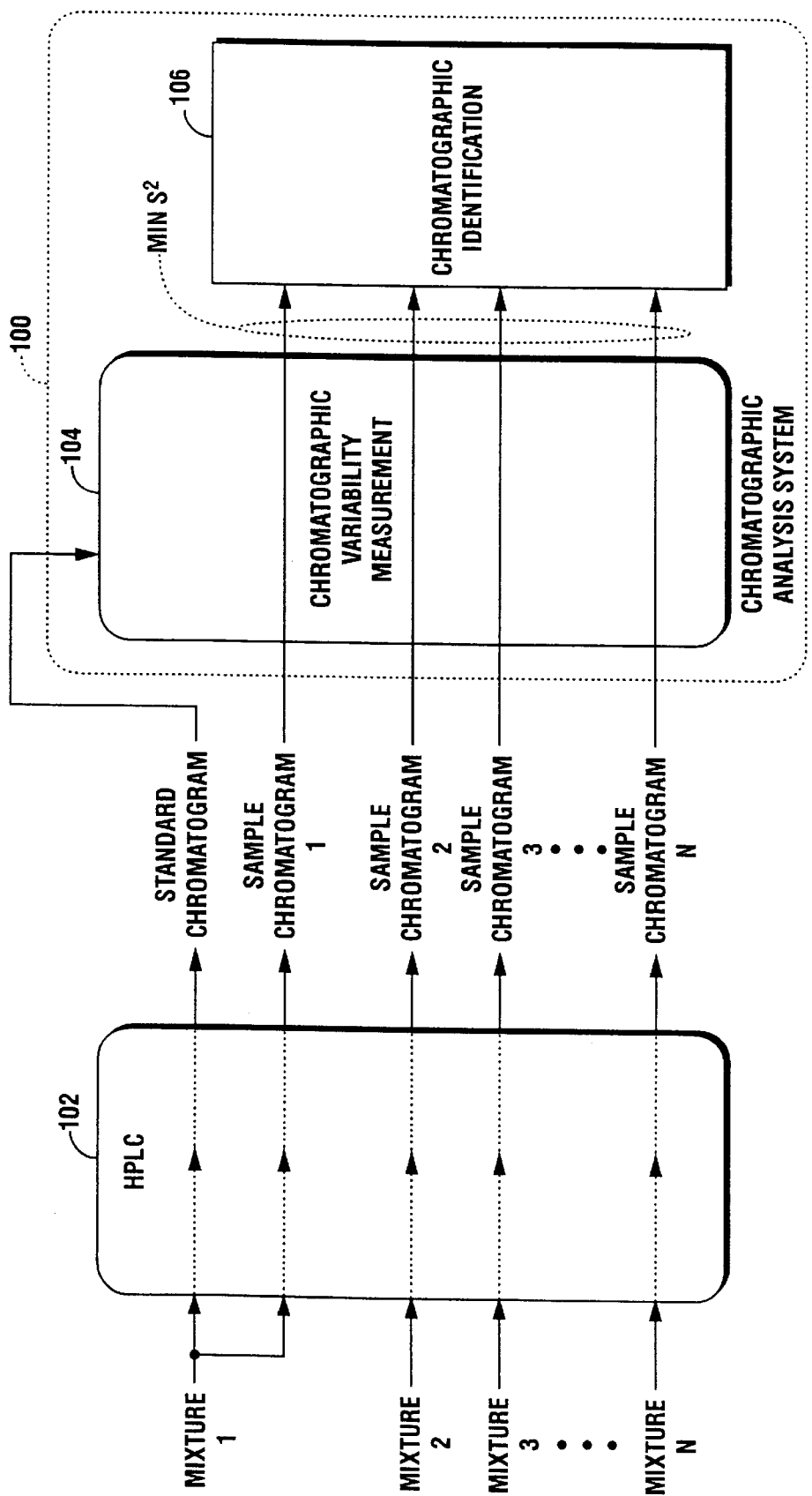
FIG. 1 is a block diagram of a preferred chromatographic analysis system coupled to an HPLC device.

FIG. 1 of the drawings shows a schematic diagram of a preferred Chromatographic Patter Analysis Device (CPAD) 100 coupled to receive data from a High-Pressure Liquid Chromatography (HPLC) system 102. An HPLC system is available from Waters Corporation, Milford, Mass. 01757 and preferably includes a pump under the trade name Waters™ 626 which continually pumps solvent through an injector, column, and detector, into a waste bottle. Such a HPLC system 102 advantageously accommodates a wide variety of applications including high-resolution protein purification, peptide mapping, nucleic acid isolations, purification and analysis of oligosaccharides and analysis of mycolic acid from mycobacteria. The injector injects a sample mixture to be separated by the column into the solvent stream generated by the pump. Preferably the injector takes the form of a Waters™ 717 plus Autosampler which may be programmed via the chromatography manager described below to perform a variety of functions including automated routines for automatically adding, mixing and injecting samples. One example of a chromatographic column which separates the components of the injected mixture is also available from Waters Corp. under the trade name Waters™ Delta-Pak™ $C_{18}$ steel column. Such a column has an inner diameter of 3.9 mm and a length of 150 mm, packed with 5 micron size beads having a 300 Angstrom pore size. The detector measures absorptivity of an eluent stream exiting the column and digitizes the measured absorbance. Such a detector is also available from Waters Corp. under the trade name Waters™ 486 Tunable UV Absorbance Detector and advantageously provides detection range from 190–600 nanometers (nm), a bandwidth of 8 nm with an accuracy of ±2 nm and a reproducibility of ±0.25 nm. The CPAD 100 is preferably implemented on a data station which controls the operation of the HPLC 102 and accepts the digitized output of the detector. Preferably, such a data station takes the form of a PC based computer configured to execute the Windows 3.1 operating system available from Microsoft Corp:, Redmond, Washington, and application programs compatible with Windows 3.1 including the Millennium® 2010 Chromatography Manager. The Millennium® 2010 Chromatography Manager (Waters Corporation, Milford, Mass.) which implements a chromatographic data management system to provide control of operation of the HPLC device 102 including the ability to program, document and link results derived from analyses performed by the device. Such a chromatography manager advantageously provides a relational database to facilitate the organization, storage and retrieval of results generated by the HPLC device 102 and a Graphical User Interface (GUI) to control data acquisition and other system operational functions.

Other types of chromatography devices may also be used in conjunction with CPAD 100 including other types of liquid chromatographs as well as gas chromatographs. CPAD 100 requires data representative of chromatograms in the form of an analog voltage signal, where typically 1 volt equals 1 absorbance unit (AU) or in the form of a digitized signal. Typically signals are sampled and digitized at the rate of once per second. Chromatographic peaks are typically 30 to 60 seconds wide as measured from the lift-off to touch-down point of an isolated peak.

As seen diagrammatically in FIG. 1, CPAD 100 generates by comparison with a standard chromatogram, via Chromatographic Variability Measurement module 104, a residual value $S^2$ for each sample chromatogram. As seen in FIG. 1, the Standard Chromatogram and Sample Chromatogram 1 are each generated from the same mixture. A plurality of additional chromatograms (seen as Sample Chromatograms 2, 3, . . . N) may be generated from Mixtures 2, 3 . . . N and transferred to the Chromatographic Identification module 106 of CPAD 100 for the purpose of determining the similarities or differences between these chromatograms and the standard. The CPAD 100 may be employed for a variety of purposes including quality control in which sample chromatograms 2, 3, . . . , N which correspond to mixtures 2, 3, . . . , N are compared to the standard chromatogram to determine differences between manufactured mixtures 2, 3, . . . , N and mixture 1 which represents a mixture having a desired composition. The CPAD 100 may also be employed for a number of other applications including mycolic acid analysis and tryptic mapping.

Figure 2:
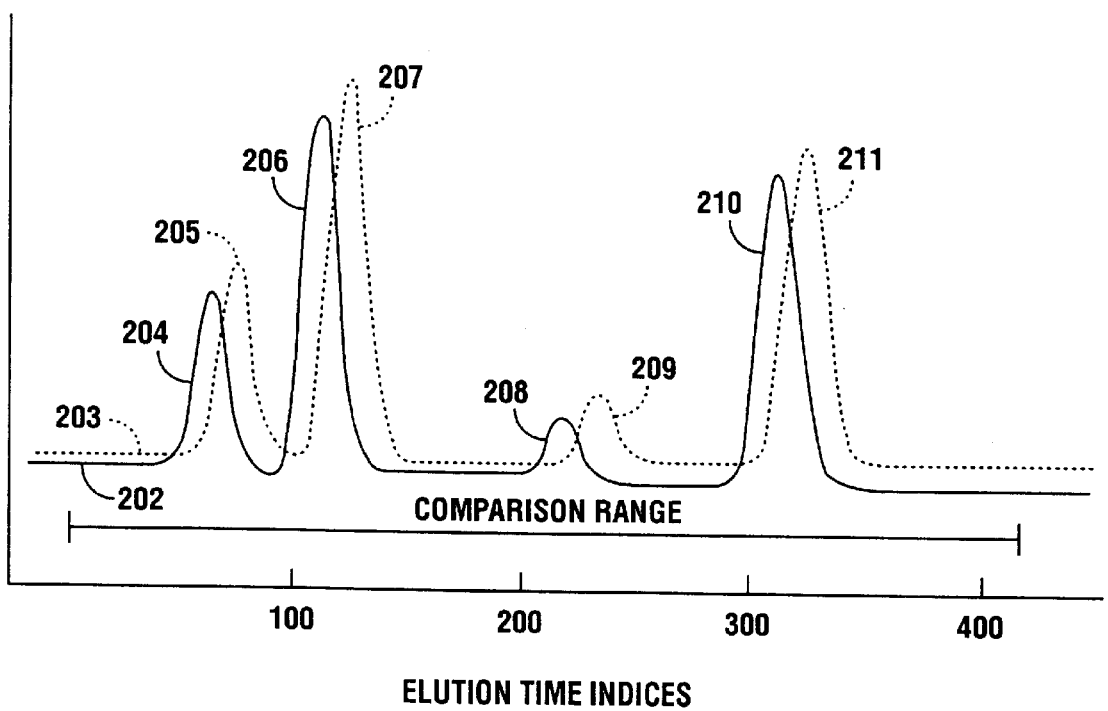
FIG. 2 is a graph showing a standard chromatogram and a sample chromatogram which are used as inputs to illustrate operation of a preferred embodiment.

FIG. 2 of the drawings illustrates the standard chromatogram and sample chromatogram 1 of FIG. 1, which will be used to illustrate the operation of a preferred embodiment. In FIG. 2, the standard chromatogram is shown in solid line 202 and sample chromatogram 1 is shown in dotted line 203. In the following explanation, various points on standard chromatogram 202 are referenced by even reference numbers 204–210 and points on sample chromatogram 203 are referenced by odd reference numbers 205–211. As seen in FIG. 2, standard and sample chromatograms 202 and 203 each include a plurality of peaks 204–211. As also seen in FIG. 2, the standard and sample chromatograms differ in a number of respects even though they are both obtained from the same mixture. For instance, the peaks of chromatogram 203 are shifted and stretched in time from the corresponding peaks of chromatogram 202. Moreover, the baseline of chromatogram 203 is shifted and sloped upward from chromatogram 202. In addition, the height of the peaks of chromatogram 203 differ from the height of corresponding peaks in chromatogram 202. As is known, such differences occur because the properties of the chromatograph itself differ slightly between injections of the same mixture. For instance, solvent flow rates in the chromatograph may change from day to day or from instrument to instrument, and baselines may drift. Table 1 below lists five common instrumental variations that affect chromatograms. In Table 1 below, the variation is listed in the leftmost column with the model value that measures the magnitude of the variation, the units of the model value and the physical sources of the variation listed in the respective columns to the right.

| Variation | Model Value | Units | Examples of Physical Origin |
| --- | --- | --- | --- |
| Concentration ratio | s | none | Changes in sample or injector |
| Retention time offset | $t_o$ | sec | Change in delay volume |
| Time scale expansion or contraction | r | sec/sec | Change in pump flow rate |
| Change in baseline offset | $b_o$ | AU | Thermal drift in the detector or eluent |
| Change in baseline drift | $b_1$ | AU/sec | Thermal drift in the detector or eluent |

CPAD 100 estimates each of the model values listed above from a comparison of the standard chromatogram with sample chromatogram 1. First, the five model values are determined to account for the difference between the two chromatograms due to chromatographic variability (referred to as "model variability"). If there is no model variability, then the model values are s=1, r=0, $t_o$=0, $b_1$=0 and $b_o$=0. Once the model variability is determined, any remaining differences, termed residual variability, are determined. As used herein, the term "residual variability" is intended to refer to differences between two chromatograms which do not arise from chromatographic variability which is described by the model defined in Table 1. The model variability and residual variability are then employed to enhance the analysis of chromatograms from different mixtures.

Before data representative of chromatograms 202 or 203 is submitted to CPAD 100 for analysis, an elution time range, also referred to as a comparison range, of the standard chromatogram, represented by the horizontal axis of the graph of FIG. 2 must be selected. The elution time range is chosen to include the peaks of interest of the standard and sample chromatographs to be compared. Preferably there is no restriction on the length of the elution time range, as long as the elution time range contains at least two peaks. Moreover, there is no restriction as the whether the peaks in the elution time range are of known or unknown compounds. For example, no peaks from a reference compound need to be included in the elution time range for the CPAD 100 to work. With two or more peaks, relative retention time shift and stretch, as well as baseline model values and concentration change can be determined. With only a single peak, retention time stretch cannot be determined. Accordingly, proper operation of the system requires inclusion of at least two peaks in the comparison range.

In the example of FIG. 2, the selected comparison range comprises four hundred points starting from point 21 and ending at point 420. In the explanation which follows, the comparison range is designated by an index $i_N$ in which $i_{start}$ designates the first point in the comparison range (point 21) and $i_{stop}$ designates the last point in the comparison range (point 420). In this example, the comparison range includes N=400 points. Moreover, in the following explanation, vectors and matrices are designated by bold characters.

In addition to a comparison range, an offset range, expressed in units of the sampling index by the parameter X, must be selected. The offset range is indicative of a maximum possible retention time offset and specifies a range from −K to +K over which the comparison between the standard and sample chromatograms is varied. Thus, the standard chromatogram is compared to 2K+1 overlapping, N-point regions of the sample chromatogram. A particular offset within the offset range is specified by a value k termed an offset index. In practice, the value 2K+1 is often comparable to the width of a chromatographic peak. In the example which follows, K=10, so offsets will range from k=+10 to k=−10 indices.

Figure 3:
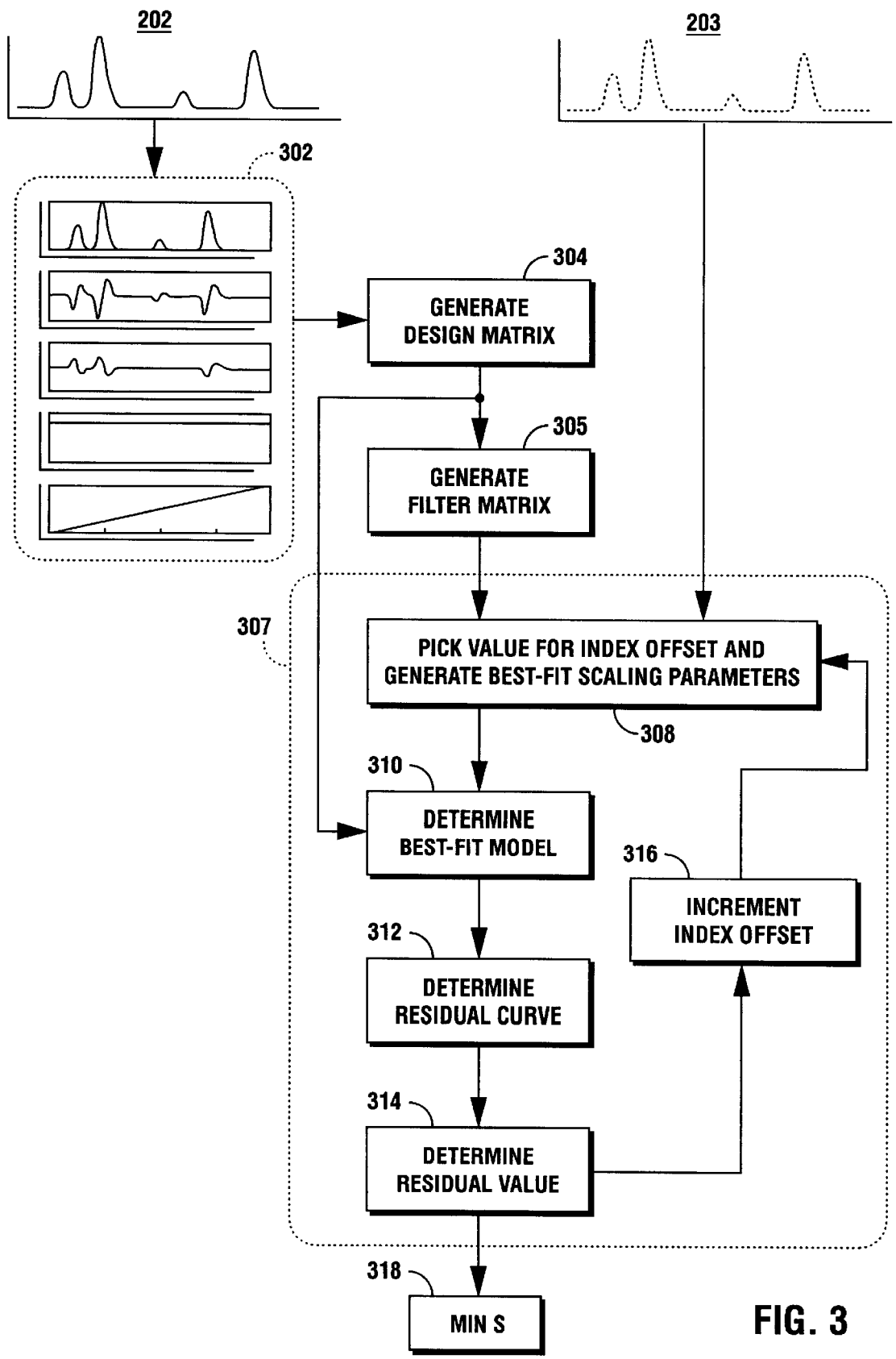
FIG. 3 is a flowchart showing the operation of a preferred embodiment.

FIG. 3 of the drawings is a flow diagram showing the steps performed by a preferred embodiment to determine chromatographic variability from standard and sample chromatograms 202 and 203. In FIG. 3, data from standard chromatogram 202 is used to generate five chromatographic variability curves which are each embodied by a corresponding set of data, herein termed "chromatographic variability data points" shown in graphical form at 302 and in greater detail in FIGS. 4(a)–4(e). Associated with each curve is the corresponding model value listed in Table 1 above. These chromatographic variability curves embody the notion of a set of chromatographics variability data points.

Figure 4A:
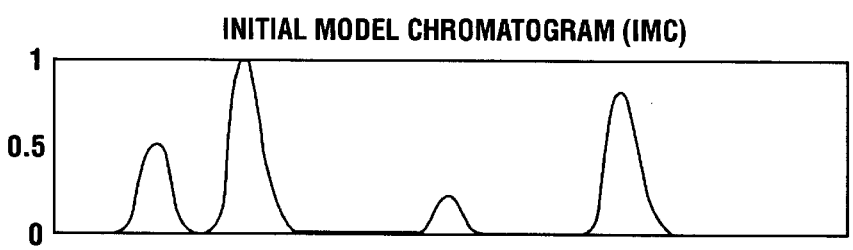
FIGS. 4(a)–4(e) are graphs showing chromatographic variability data points generated by a preferred embodiment as a function of the standard chromatogram of FIG. 2.

The data points seen in FIG. 4(a) are generated by subtracting from the standard chromatogram, the minimum absorbance measured within the selected elution time range. The minimum absorbance measured within the selected elution time range can be found by collecting and sorting all the absorbance values from within that time range, and picking the lowest value from this sorted set. The resulting curve seen in FIG. 4(a) is referred to as an Initial Model Chromatogram (IMC) and the associated scaling parameter is referred to as s which operates to model a change in concentration of the standard. The N elements of the IMC are labeled by $p_i$, where i=1, . . . , N.

Figure 4B:
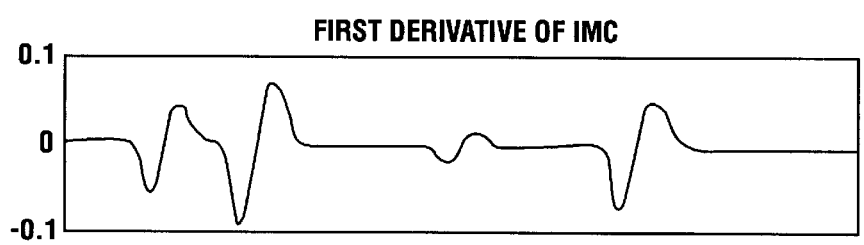

The data points seen in FIG. 4(b) are generated by taking the first derivative of the IMC. Preferably such an operation is performed with the use of a Savitzky-Golay filter as described by Abraham Savitzky and Marcel J. E. Golay in a paper entitled "Smoothing and Differentiation of Data by Simplified Least Squares Procedures" *Analytical Chemistry*, v. 36, pp. 1627–1639 (July 1964).

The N elements of the curve of FIG. 4(b) are labeled $p'_1$. The scaling parameter associated with this curve is $\delta$. Adding the scaled elements of the curve of FIG. 4(b) to the IMC models a shift in the peak retention of the IMC by a time equal to $t_0 = \delta/s$.

Figure 4C:
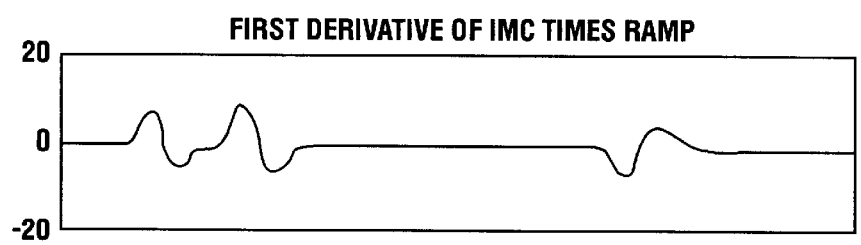

The data points seen in FIG. 4(c) are generated by taking the element-by-element product of the curve of FIG. 4(b) with a line of unit slope and zero mean. Specifically, if there are N points within the elution time range, then $t_i = -h, \ldots, -1, 0, 1, \ldots, h$ defines a curve that has unit slope and zero mean, where $h=(N-1)/2$. The scaling parameter associated with this curve is r. Adding the scaled elements of the curve of FIG. 4(c) to the IMC models a stretch in the retention times of peaks in the IMC about the IMC's midpoint. The retention time of a peak is then proportional to r times the difference between its retention time and the midpoint of the comparison range.

Figure 4D:
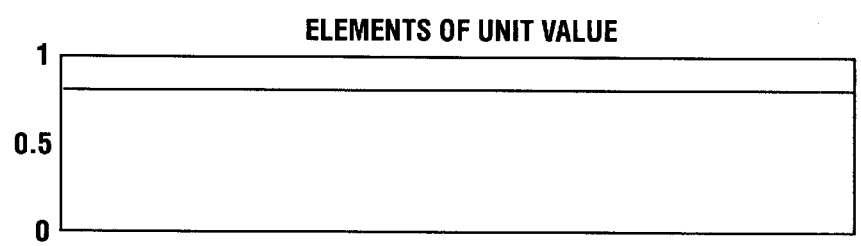
Figure 4E:
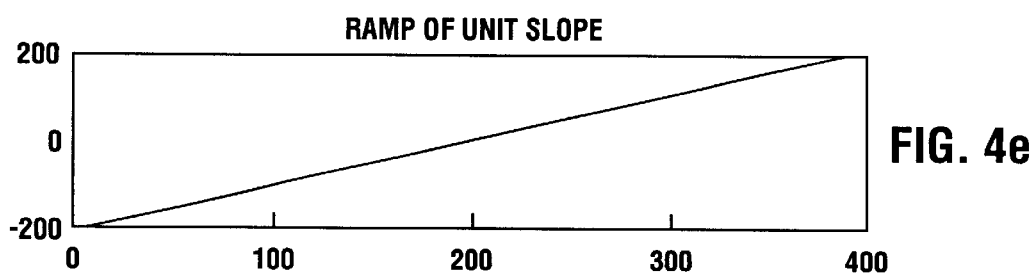

The curve of FIG. 4(d) is a line having zero slope and a unit value. The scaling parameter associated with this curve is $b_0$. Adding the scaled elements of the curve of FIG. 4(d) to the IMC models a change in the baseline of the IMC by an amount equal to $b_0$. The curve of FIG. 4(e) is a line of unit slope and zero mean. The elements of this curve are the points $t_i$ defined above. The scaling parameter associated with this curve is $b_1$. Adding the scaled elements of the curve of FIG. 4(e) to the IMC models a change in the baseline slope of the IMC by an amount equal to $b_1$.

Once the chromatographic variability curves are generated, the CPAD generated at 304 a design matrix with N rows and five columns. Thus in the present example, the elements of the design matrix consist of 400 rows and five columns. The elements of the design matrix are denoted by $D_{ij}$ where i ranges from 1 to 400 and j ranges from 1 to 5. Each column of the design matrix therefore also corresponds to a scaling parameter. Each element of the design matrix is a point along one of the chromatographic variability curves. Preferably this same design matrix is associated with the standard chromatogram and is used for all values of k, which as explained above specifies an index offset.

From the design matrix (D), a filter matrix (F) is generated in accordance with the following relationship:

$$F = (D^t D)^{-1} D^t \qquad (1)$$

The filter matrix has 5 rows and N columns. Each row of the filter matrix is an N element row-vector that acts as a projection vector associated with the respective chromatographic variability curve. In the above equation, the prime indicates matrix transposition, and the −1 indicates matrix inversion. As will be understood by those skilled in the art in view of the present disclosure, the equation (1) above, advantageously implements a solution to the linear least-squares problem of fitting of the sample data to the scaled columns of the design matrix. In other words, the relationship expressed in equation (1) above, when combined with the relationships shown in equations (2), (3) and (5) below provides a set of values for the five scaling parameters (s, $\delta$, r, $b_0$, $b_1$) that give the lowest value of $S_k^2$. Alternatively, such values may be carried out by a search over a five-dimensional space, or by some iterative means, again in a five-dimensional space.

After the filter matrix is generated, a value for the offset range K is selected, and the functions shown within block 307 are performed for each index offset value k. For each index offset k, the functions within block 307 generate quantities which are indicative of the difference between the standard and sample chromatograms for that index offset k.

At step 308, best fit scaling parameters are generated as a function of the filter matrix, the sample chromatogram and the offset index k, as follows The best fit parameters for offset index k are preferably generated by choosing absorbances from the sample chromatogram that correspond to the comparison range, offset by offset index k. Thus if the comparison range is from indices that range from $i_{start}$ to $i_{stop}$ then the sample chromatogram contains elements from $i_{start}+k$ to $i_{stop}+k$, which are designated by the element q. In Block 308, we solve the least-squares problem of finding the vector $c^k$ that minimizes the quantity:

$$\|Dc^k - q^k\|^2 \quad (2)$$

The product $Dc^k$ has the effect of weighting the columns of D with the five elements of the vector $c^k$. In this example, $c^k$ is a five element column vector, whose values are the scaling factors. This product $Dc^k$ is a model for the chromatographic data $q^k$ based on the chromatographic variability curves. The vector $q^k$ contains the sample absorbances $q^k_j$. Finding the vector $c^k$ that minimizes the above quantity gives a least-squares solution to the above equation provides a model that best fits the sample chromatographic data offset by k. The well known solution that gives the vector $c^k$ that minimizes the quantity above is obtained from the filter matrix F in accordance with the following relationship:

$$c^k = Fq^k \quad (3)$$

This well known formulation and solution to the least-squares problem can be found in a book by Gilbert Strang entitled "Introduction to Applied Mathematics" published by Wellesley-Cambridge Press, Wellesley, Mass. 02182 USA (1986) on page 37. The five elements of the column vector $c^k$ are the least-squares estimates of each of the scaling parameters (s, δ, r, $b_1$, $b_0$) and are associated as follows:

$$s = c_1^k$$
$$\delta = c_2^k$$
$$r = c_3^k \quad (4)$$
$$b_0 = c_4^k$$
$$b_1 c_5^k$$

A best-fit model for the selected index k is then generated at step 310 by generating a column vector $m_i$, with a length equal to the number of points in the comparison range (400 in the present example), in accordance with the following relationship:

$$m^k = Dc^k \quad (5)$$

The effect of the matrix multiplication seen above in equation (5) is to weight the columns of $D_{ij}$ with the parameter values $c^k$, and sum the result. The resulting sum is the model $m^k$ composing a set of 400 points which embody a model chromatogram that best fits the sample chromatogram, offset by k.

At step 312, the model chromatogram ($m_i$) is compared to the sample chromatogram ($q_i^k$) by obtaining the difference between the two curves to form a residual curve ($r_i = m_i - q_i$). The quantity $r_i$ is the point-to-point difference between the model and the sample. From the residual curve, at step 314, the sum of the squared residuals ($S^2$), also termed the residual value, which measures the precision of the fit of the sample to the model, is then generated in accordance with the following relationship:

$$S_k^2 = \sum_{i=1}^{N} (m_i^k - q_i^k)^2 \quad (6)$$

The right hand side of equation (6) is equivalent to the combination of equations (2) and (5).

The value $S^2_k$ may also be normalized in accordance with the relationship shown in equation (7) below to a value $R_k$ which expresses $S^2_k$ as the percentage deviation between the model and the sample chromatogram:

$$R_k = 100 \times \sqrt{\frac{S_k^2}{\sum_{i=1}^{N} q_i^2}} \quad (7)$$

Once the residual value is generated at step 314, then the offset index is incremented at 314 and the steps 308–314 are repeated for each offset index in the range. The offset index value is initially chosen to be −k and is then incremented for each subsequent pass through steps 308, 310, 312 and 314 until an 52 value has been generated for each index offset value. While the offset index value is changed in FIG. 3 by incrementing it, other methods of changing the value, such as decrementing from k may be used. At 318, once a value to herein $S_k^2$ is generated for each offset index, the lowest value is selected, which is referred to herein as $S^2$ or min $S^2$. This lowest value identifies the best-fit value $k^*$ and the parameters associated with $k^*$.

The method used to measure $S^2$ is significant, because of the behavior of $S^2$ when the chromatograms are of the same mixture. Because $S^2$ measures differences after removing the effects of concentration change and chromatographic variability, a low value is obtained for $S^2$ and one characteristic of the system residual errors.

FIGS. 6(*a*)–6(*d*) show an example of the best-fit model for an offset index of k =0. In FIG. 6(*a*), the IMC (solid line) and the sample chromatogram (dotted line), offset by k =0 points are shown. In FIG. 6(*b*) the IMC (solid line) and the best-fit model (dotted line) that best fits the sample offset by k=0 points is shown. FIG. 6(*c*) shows the best-fit model, (dotted line) and the sample (solid line). From these two curves a relative deviation ($R_d$) is obtained of $R_d$=15.8%. FIG. 6(*d*) shows a plot of the residuals, which are point-to-point differences between the sample and the model chromatograms of FIG. 6(*c*). The sum of the squares of the values in FIG. 6(*d*) gives the value for $S^2$.

FIGS. 7(*a*)–7(*d*) are similar to FIGS. 6(*a*)–6(*d*) but show an example of the best-fit model for an offset index of k=4. The IMC (solid line) and the sample (dotted line) are shown in FIG. 6(*a*), and the IMC (solid line) and the best-fit model (dotted line) are shown in FIG. 6(*b*). FIG. 6(*c*) shows the best-fit model (solid line) and the sample (dotted line). From these two curves, a relative deviation of $R_4$ =4% is obtained. As can be seen, an effect of k=4 produces a better fit than an offset of k=0. FIG. 7(*d*) shows a plot of the residuals. As with FIG. 6(*d*), the sum of the squares of the values in this plot gives the value for $S^2$.

Figure 5:
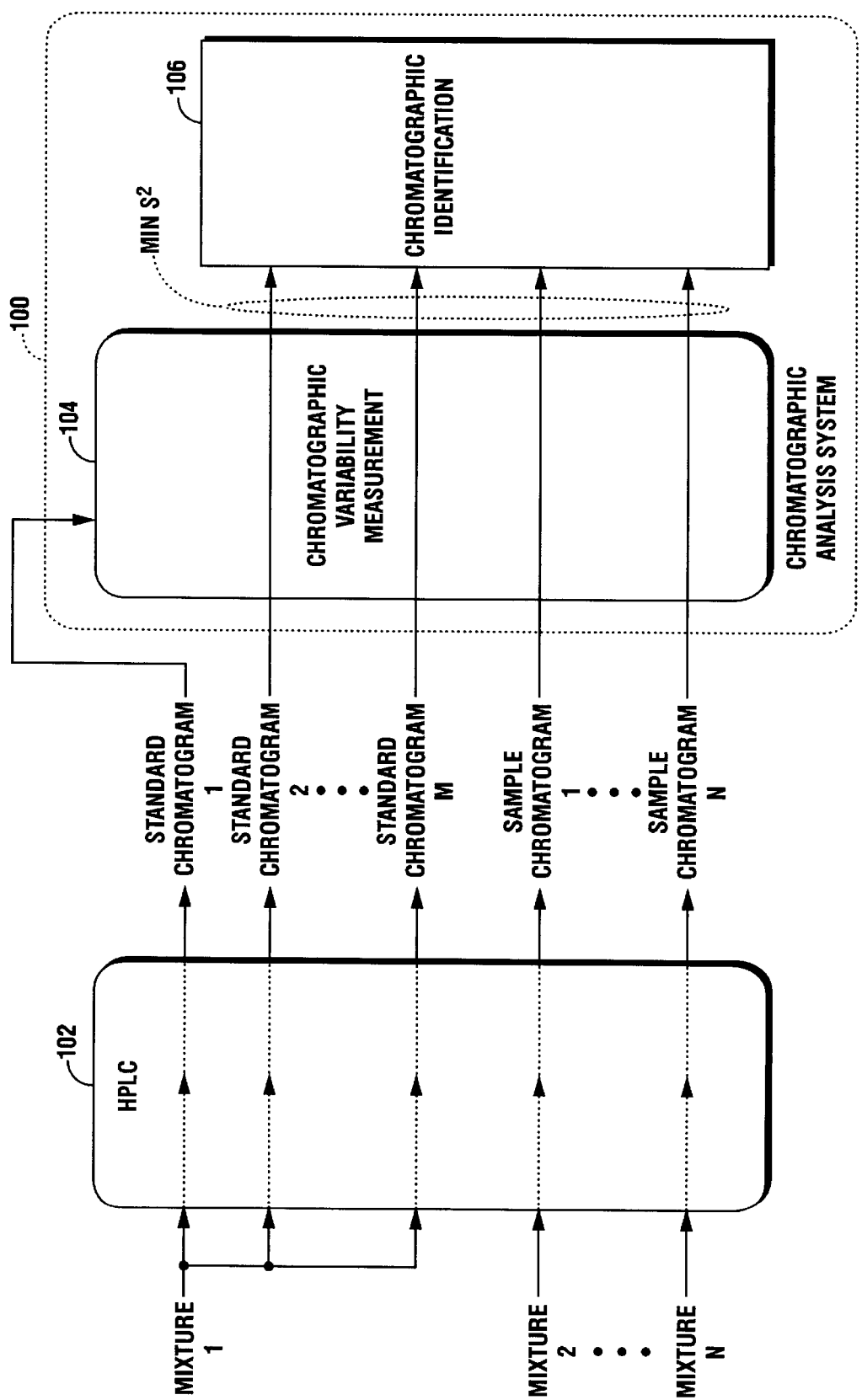
FIG. 5 is a block diagram of an alternative use of the system shown in FIG. 1.
Figure 6A:
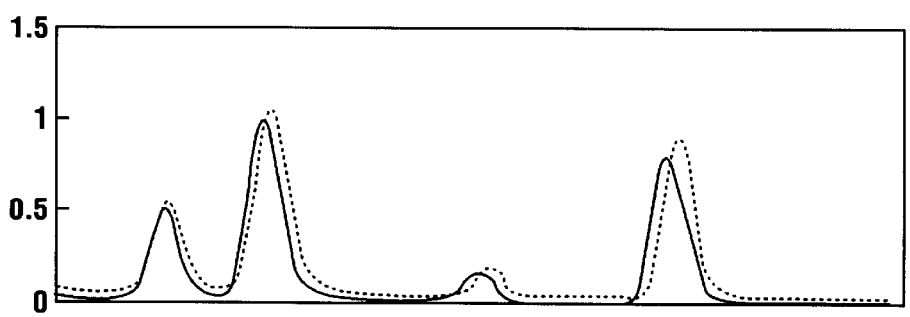
FIGS. 6(a)–6(d), and 7(a)–7(d), are graphs illustrating operation of a preferred embodiment for different offset values.
Figure 6B:
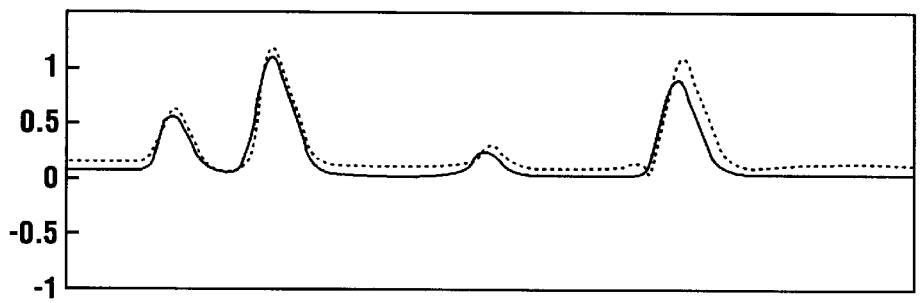
Figure 6C:
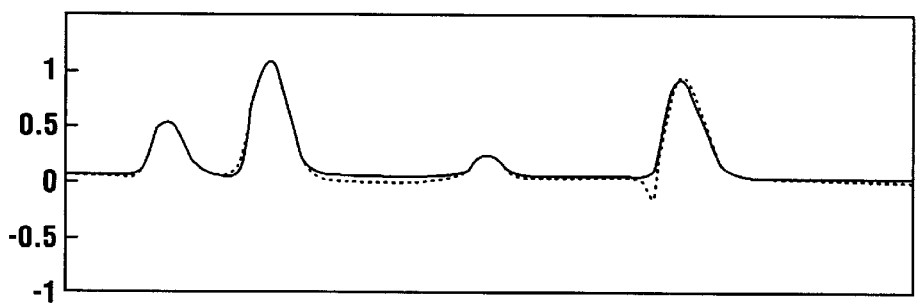
Figure 6D:
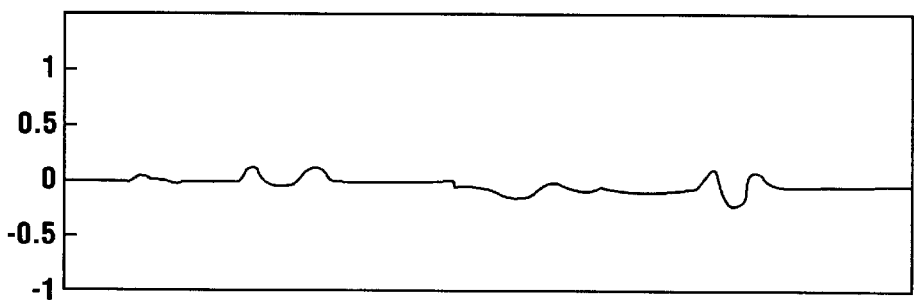
Figure 7A:
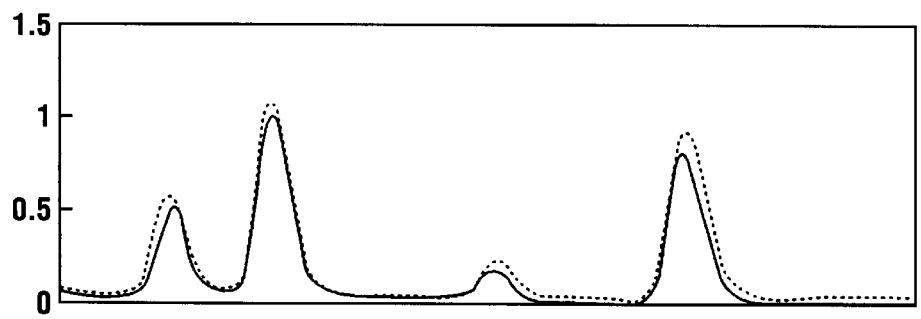
Figure 7B:
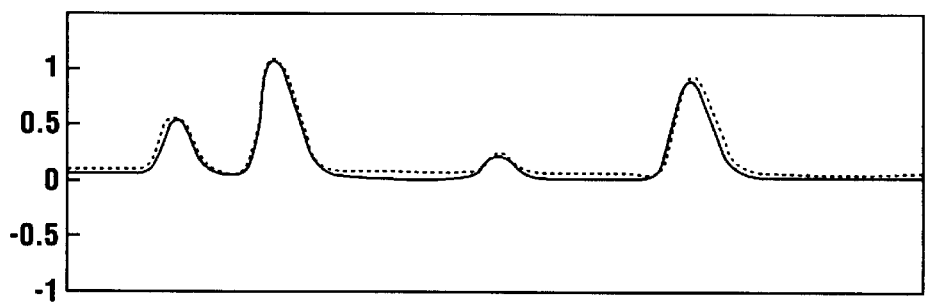
Figure 7C:
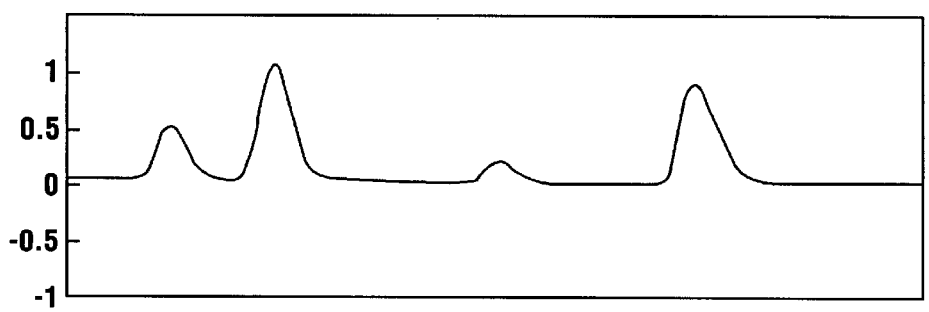
Figure 7D:
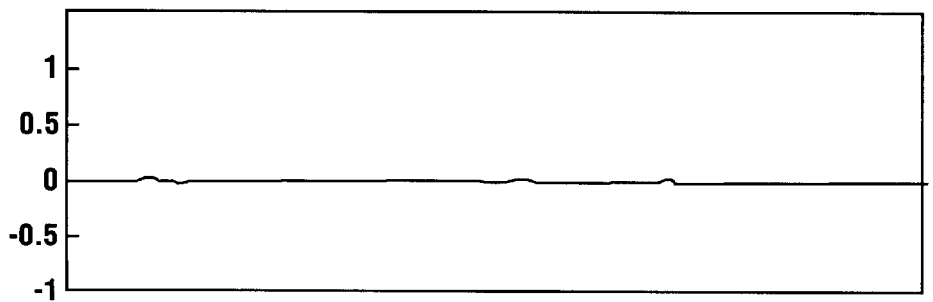

The value min $S^2$ is also a measure of the difference between a pair of chromatograms, whether they are from the same or different mixtures. Once such a determination of chromatographic variability has been generated from comparison of chromatograms obtained from the same or similar mixture, chromatograms of different mixtures may be compared to the standard chromatogram to determine if a different mixture is the same or different from the mixture corresponding to the standard chromatogram. Often times the standard mixture, often referred to as a reference standard or a gold standard, from which the standard chromatogram is obtained, is carefully stored, and only small amounts of the reference standard are used, perhaps on a weekly basis, as part of comparison assays. An analyst may generate one or more chromatograms from the reference standard for comparison with newly manufactured mixtures. In the simplest case, described above with reference to FIGS. 1–3, two chromatograms are generated from the reference standard mixture: the standard chromatogram and the sample chromatogram. Oftentimes however, a plurality (N) of chromatograms are generated from the reference standard as shown in FIG. 5. As seen in FIG. 5 a plurality of standard chromatograms (standard chromatograms 1,2, . . . , M) are generated from Mixture 1 which is the reference mixture. By obtaining M chromatograms from one mixture, a statistically significant distribution of $S^2$ values can be generated and chromatograms with large deviations from the distribution values can be rejected. Other data gathering strategies are also possible. For example, in the case of clinical studies, when mixtures are from biologic sources, multiple reference mixtures may be used. In general, the problem of determining whether a value is or is not part of a distribution is a well known problem in statistics. Possible solutions to this problem are described by J. C. Miller and J. N. Miller in "Statistics for Analytical Chemistry" published by Halsted Press: a division of John Wiley & Sons, New York (1988).

As shown in FIG. 1 and explained in the accompanying description, an arbitrary number of unknown or sample mixtures may be used. In the simplest scenario, shown in FIG. 1, one reference standard mixture is used (Mixture 1), from which two chromatograms are obtained (Standard Chromatogram and Sample Chromatogram 1), and multiple unknown mixtures are used (Mixtures 2, 3, . . . , N) for which one chromatogram each is obtained (Sample Chromatograms 2, 3,. . . , N). In such a scenario, as further described in FIGS. 2 and 3, a set of five variability curves, five scaling parameters, an integer offset, and a residual value are generated from the comparison of the standard chromatograms and sample chromatogram 1. The residual value min $S^2$ is stored, and in the following description is referred to as the reference residual. From the reference residual a threshold value which is indicative of a maximum acceptable deviation from the standard is generated by a technique appropriate for the application. For example, the threshold value might be some multiple of the reference residual, or alternatively, might be a fixed value. The threshold value may also be generated from an analysis of the distribution of reference residuals generated from a comparison of a plurality of sample chromatograms, generated from the same mixture as the standard, to the standard chromatogram.

Next, the standard chromatogram is compared to one of the unknown (sample) chromatograms. Using the five variability curves generated from the standard, a new set of five scaling parameters, a new integer offset value, a new residual curve and a new residual value min $S^2$ is generated for each sample. Finally, the residual values obtained for each of the samples (the unknown residuals) is compared to the threshold. If the unknown residual is greater than the threshold, then the mixture corresponding to that residual is determined to be different from the standard mixture. If the unknown residual is less than the threshold, then the unknown is determined to be the same (or, strictly speaking, not discernibly different from) the standard.

While the foregoing discussion has focused on an explanation how of a single N-point chromatographic comparison region of a standard chromatogram is compared to 2K+1 overlapping, N-point regions of a sample chromatogram, alternatives, as alluded to above exist. For example, the techniques described above could be applied to multiple, overlapping or non-overlapping comparison ranges or portions of data from each chromatogram. One mode of comparison found to be useful in the comparison of tryptic maps is to pick a comparison range that is about five or six peak widths wide, and perform comparisons using a series of such comparison ranges displaced by only a fraction of a peak width. For example, the comparison range could be 150 points, and the comparison range could be moved only by about one to five points, so each point of data is included in approximately thirty to 150 successive comparison ranges. Each such comparison range within the standard chromatogram is, again, compared to its respective 2K+1, overlapping N-point regions within the sample chromatogram, as described previously. With such a comparison herein termed a "moving window comparison", the residual values may be plotted as a function of the enter position of each comparison range. The residual values may also be combined into a single composite value. In addition, one or more scale values each derived from individual comparisons may be plotted as a function of the central point of each comparison range.

Another variable to the above description which is contemplated is the use of less than the five variability parameters reflected in the five variability curves and the five scaling parameters. In general, the advantage of retaining only a subset of the five variability parameters is that the residual difference curves and values for R and $S^2$ are made more sensitive to those variations in the sample mixture that are reflected in the sample chromatogram. Also, the computational time needed for each comparison is reduced. This reduction can be useful in the case of moving window comparisons which are computationally intensive. However, enough parameters must be included so as to properly model the components of chromatographic variability that are present. For example, when the comparison region is short, only a few peak widths wide, it may be possible to use a model that includes only three variability parameters, with the corresponding three variability curves and the three scaling parameters. The preferred choice would be the scale factor parameterized by s, the retention time offset parameterized by $\delta$, and the baseline offset parameterized by $b_0$. Over a short comparison region, the remaining two variabilities, retention time stretch, parameterized by r, and baseline slope, parameterized by $b_1$ may be small enough so as not to be significant. A fourth variable consisting of either retention time stretch or baseline slope may be added to the foregoing subset if the variations due to these effects, as produced by the chromatograph, warrant the addition.

An additional subset consists of the single variability parameter, the scale s. For this subset to be appropriate the baseline offsets and slopes must be nearly the same for each comparison region, and there must be little or no retention time stretch. Such a method may be less advantageous than the three parameter, four parameter or five parameter models described above. In particular, this method gives a value of retention time offset that equals a integral number of sample periods or index offsets. However, this method still has the advantage that it measures a retention time offset with out requiring the identification or characterization of peaks. Also, this method has the advantage of giving a value for the ratio of concentrations, described by the scale change s, a residual curve and residual value $S^2$. The disadvantage of the preceding one parameter method is that retention time shifts will in general not correspond to an integral number of sample periods or index offsets. We can improve the preceding method that uses the one variability parameter s, by adding to it the parameter δ and corresponding curve associated with a retention time shift. This two-parameter method, when comparing curves that are offset by other then an integral number of sampling units, will interpolate between integral index offsets and thereby accurately measure retention time shift. In addition, this two-parameter method retains the advantage of producing a residual curve and a value for $S^2$. In summary, the useful subsets of the five parameters are the subset consisting of s, the subset consisting of s and δ, the subset consisting of s, δ, and $b_0$, the subset consisting of s, δ, $b_0$ and r, and the full set of parameters, s, δ, $b_0$, r and $b_1$.

The embodiment described in connection with FIGS. 1, 2 and 3 is preferably implemented as a program executing on a general purpose computer. A code listing of a preferred implementation in the MATLAB® programming language, is provided below. The below listing may be converted to executable form by interpretation via an appropriate interpreter for the MATLAB® programming language available from The Math Works, Inc., Natick, Mass. 01760. Copyright 1996 Waters Corp.

```
%AlgnCode   Alignment demo
%
%    [Chi Square, BestIndOffset, SampleModel, LinearParameters, ...
%           Residuals, StanOffset, Angle, PercentRSD] = ...
%       PM_T_Off(StandardPattern,DerivStanPattern,
%       StanIndToMatch, ...
%       SamplePattern, IndOffset,Model)
%    Inputs (all must be row vectors)
%    StanIndToMatch     index vector of library elements involved
%    in match IndQffset     vector of offset indices
%
%
%    Outputs:
%    ChiSquare        Minimum for all search ranges
%    BestIndOffset    Best index offset corresponding to ChiSquare
%    SampleModel      Sample model
%    LinearParameters    Absorbance scale, Time offset, Time stretch,
Baseline Offset
%    Residuals
%    StanOffset    Absorbance offset
%    Angle         Constrast angle.
%    PercentRSD    Percentage deviation between library and sample
function    [ChiSquare, BestIndOffset, SampleModel,
    BestLinearParameters, ...
    Residuals, StanOffset, Angle, PercentRSD] = ...
    AlgnCode(StandardPattern,DerivStanPattern, ...
    StanIndToMatch, ...
    SamplePattern, IndOffset,Model)
% Qualification of data
[n1,d]=size(StandardPattern);
[n2,NumInd]=size(StanIndToMatch);
[n3,d]=size(SamplePattern);
[n4,d]=size(IndOffset);
if~(n1==1 & n2==1 & n3==1 & n4==1)
    error('All inputs must be row vectors')
end
% Sizes
numOffsets = length(IndOffset);
ChiSquare Vec = zeros(1,numOffsets);
LenPattern = length(StanIndToMatch);
%Design matrix:
% Prepare Standard Pattern by selecting elements and autozeroing
StanPatternToMatch = StandardPattern(StanIndToMatch);
StanOffset      = min(StanPatternToMatch);
StanPatternToMatch = StanPatternToMatch - StanOffset;
maxStan         = max(StanPatternToMatch);
StanPatternToMatch = StanPatternToMatch/maxStan;
DerivStanPattern            = DerivStanPattern/maxStan;
% Obtain partials w/r to time and time scale
DerivStanPatternToMatch = DerivStanPattern(StanIndToMatch);
Ramp          = 1:LenPattern;
Ramp          = Ramp - mean(Ramp);      %- LenPattern/2 to + LenPattern/2
ScaleStanPatternToMatch = DerivStanPattern(StanIndToMatch) * Ramp;
% Baseline
BaselineOffset = ones(size(StanPatternToMatch'));
% Autozero Sample at midpoint of search range.
SampleOffset  =
min(SamplePattern(StanIndToMatch+floor(mean(Indoffset))));
SamplePattern = SamplePattern - SampleOffset;
SampleMax     =
max(SamplePattern(StanIndToMatch+floor(mean(IndOffset))));
SamplePattern = SamplePattern/SampleMax;
% Design matrix
% Five parameter model, Absorbance scale, time offset, time scale,
baseline offset, slope
    Design = [StanPatternToMatch', ...
            DerivStanPatternToMatch',...
            ScaleStanPatternToMatch',
            BaselineOffset,
            Ramp'];
% Least Squares solution:
ProjMatrix  = inv(Design'*Design) *Design';
% Build up SampleMatrix for each index offset
SampleMatrix = zeros(LenPattern,numOffsets);
for ii = 1:numOffsets
    SampleMatrix(:,ii)   = SamplePattern(StanIndToMatch+IndOffset
(ii))'; end
%%%%%%%%%%%%%%%%%%%%%%%%%%%%%%%%%%%%%%
%%%%%
%   Vectorized Computation
%%%%%%%%%%%%%%%%%%%%%%%%%%%%%%%%%%%%%%%
% Best fit linear parameters for each index offset.
%NumParam x numOffsets  = (NumParam x LenPattern) * (LenPattern x
numOffsets)
LinearParameters    = ProjMatrix * SampleMatrix;
% LenPattern x numOffsets = LenPat x numOff - (LenPat x
Numparam)* (NumP x numOff)
ModelCurves   = Design*LinearParameters;
Residuals     = SampleMatrix - ModelCurves;
% numOff x NumOff = (numOff x LenPat)*(LenPat x numOff);
ChiSquareVec       = sum(Residuals * Residuals);
% Search for best Least squares solution:
[ChiSquare, iiBest]     = min(ChiSquareVec);
% Report results for best fit
BestIndOffset  = IndOffset(iiBest);
SampleModel    = SampleMatrix(:,iiBest)'+ SampleOffset;
BestLinearParameters = LinearParameters(:,iiBest);
Residuals      = Residuals(:,iiBest)';
Angle    = (180/pi)*asin(sqrt(ChiSquare)/norm(SampleMatrix(:,iiBest)));
PercentRSD     = 100*sqrt(ChiSquareVec/sum(StanPatternToMatch.^2));
```

It is to be understood that the specific mechanisms and techniques which have been described are merely illustrative of one application of the principles of the invention. Numerous modifications may be made to the methods and apparatus described without departing from the true spirit and scope of the invention.

What is claimed is:

1. A device for increasing accuracy of analysis of a sample, comprising:

a first apparatus configured to receive a standard for chromatographic analysis and to generate a standard chromatographic test result represented by a set of standard chromatographic data indicative of said standard, said first apparatus being further configured to receive a sample for chromatographic analysis and to generate a sample chromatographic test result represented by a set of sample data indicative of said sample chromatographic test result, said standard chromatographic data and said sample data being generated by sampling each of said sample and said standard at a fixed rate;

a processor for receiving said standard chromatographic data from said first apparatus and generating at least one set of variability data, from said standard chromatographic data said at least one set of variability data indicative of effects of a predetermined source of variability of said first apparatus on said standard chromatographic test result, said processor further generating a set of modified standard chromatographic data, corresponding to said standard chromatographic data modified as a function of said at least one set of variability data, in order to model variability of said sample chromatographic test result from said first apparatus.

2. A device as set forth in claim 1 further comprising means, responsive to said modified standard chromatographic data and to said sample chromatographic data for generating a residual value, indicative of differences between said modified standard chromatographic data and said sample chromatographic data.

3. A device as set forth in claim 2 comprising:

means, responsive to said at least one set of variability data and to said sample chromatographic data, for generating at least one scaling parameter, said at least on scaling parameter corresponding to said at least one set of variability data; and means for generating said set of modified standard chromatographic data by altering said at least one set of variability data as a function of said at least one scaling parameter.

4. A device as set forth in claim 2 comprising:

means, responsive to a selected offset index range, indicative of an amount by which said standard chromatographic data may be shifted, for generating a plurality of sets of said at least one scaling parameter as a function of said at least one set of variability data and a corresponding set of standard chromatographic data obtained from said standard chromatographic data shifted by an offset index value within said selected offset index range;

means for generating sets of said modified standard chromatographic data by altering said at least one set of variability data as a function of each of said plurality of sets of said scaling parameter;

means for generating said residual value for each of said set of modified standard chromatographic data;

means for selecting a set of modified sample chromatographic data as a function of the set of modified standard chromatographic data having the lowest residual value.

5. A device as set forth in claim 4 wherein said at least one scaling parameter comprises:

a first scaling parameter indicative of a change in concentration attributable to variability of said first apparatus.

\* \* \* \* \*